United States Patent
Sekimoto et al.

(10) Patent No.: US 9,250,174 B2
(45) Date of Patent: Feb. 2, 2016

(54) PARTICLE COUNTING SYSTEM

(71) Applicant: RION CO., LTD., Tokyo (JP)

(72) Inventors: Kazuma Sekimoto, Tokyo (JP); Kazuo Ichijyo, Tokyo (JP)

(73) Assignee: RION CO., LTD., Tokyo (JP)

( * ) Notice: Subject to any disclaimer, the term of this patent is extended or adjusted under 35 U.S.C. 154(b) by 0 days.

(21) Appl. No.: 14/410,620

(22) PCT Filed: Jun. 25, 2013

(86) PCT No.: PCT/JP2013/003966
§ 371 (c)(1),
(2) Date: Dec. 23, 2014

(87) PCT Pub. No.: WO2014/002484
PCT Pub. Date: Jan. 3, 2014

(65) Prior Publication Data
US 2015/0211977 A1 Jul. 30, 2015

(30) Foreign Application Priority Data
Jun. 27, 2012 (JP) .................................. 2012-143840

(51) Int. Cl.
*G01N 15/14* (2006.01)
*G01N 15/10* (2006.01)
(Continued)

(52) U.S. Cl.
CPC ............ *G01N 15/1404* (2013.01); *G01N 15/10* (2013.01); *G01N 15/1434* (2013.01); *G01N 15/1459* (2013.01); *G01N 15/06* (2013.01); *G01N 2001/2223* (2013.01); *G01N 2015/0046* (2013.01); *G01N 2015/0693* (2013.01); *G01N 2015/1486* (2013.01)

(58) Field of Classification Search
USPC ............ 356/355–343, 423–437; 422/186.04, 422/186.07, 186.18, 73, 99; 435/34, 288.7, 435/287.1, 287.2, 309.1, 30
See application file for complete search history.

(56) References Cited

U.S. PATENT DOCUMENTS 6,217,636 B1 * 4/2001 McFarland ...................... 95/216
6,544,484 B1 * 4/2003 Kaufman et al. ........ 422/186.04
(Continued)

FOREIGN PATENT DOCUMENTS

JP     S59-224542     12/1984
JP     H07-113739     5/1995
(Continued)

OTHER PUBLICATIONS

International Search Report dated Aug. 6, 2013, which issued during prosecution of International Application No. PCT/JP2013/003966, which corresponds to the present application.

*Primary Examiner* — Sang Nguyen
(74) *Attorney, Agent, or Firm* — Troutman Sanders LLP

(57) ABSTRACT

A particle counting system includes a collector, a liquid input/output operation executing means, and a particle counter. The collector performs a collecting operation to introduce the surrounding air into a container storing a liquid to collect airborne particles in the liquid. The liquid input/output operation executing means executes a series of liquid input/output operations to supply an additional liquid for the collecting operation to the collector and discharge the liquid after the collecting operation from the collector. The particle counter measures the number of particles contained in the liquid discharged from the collector with the series of liquid input/output operations.

12 Claims, 7 Drawing Sheets

Figure 1:
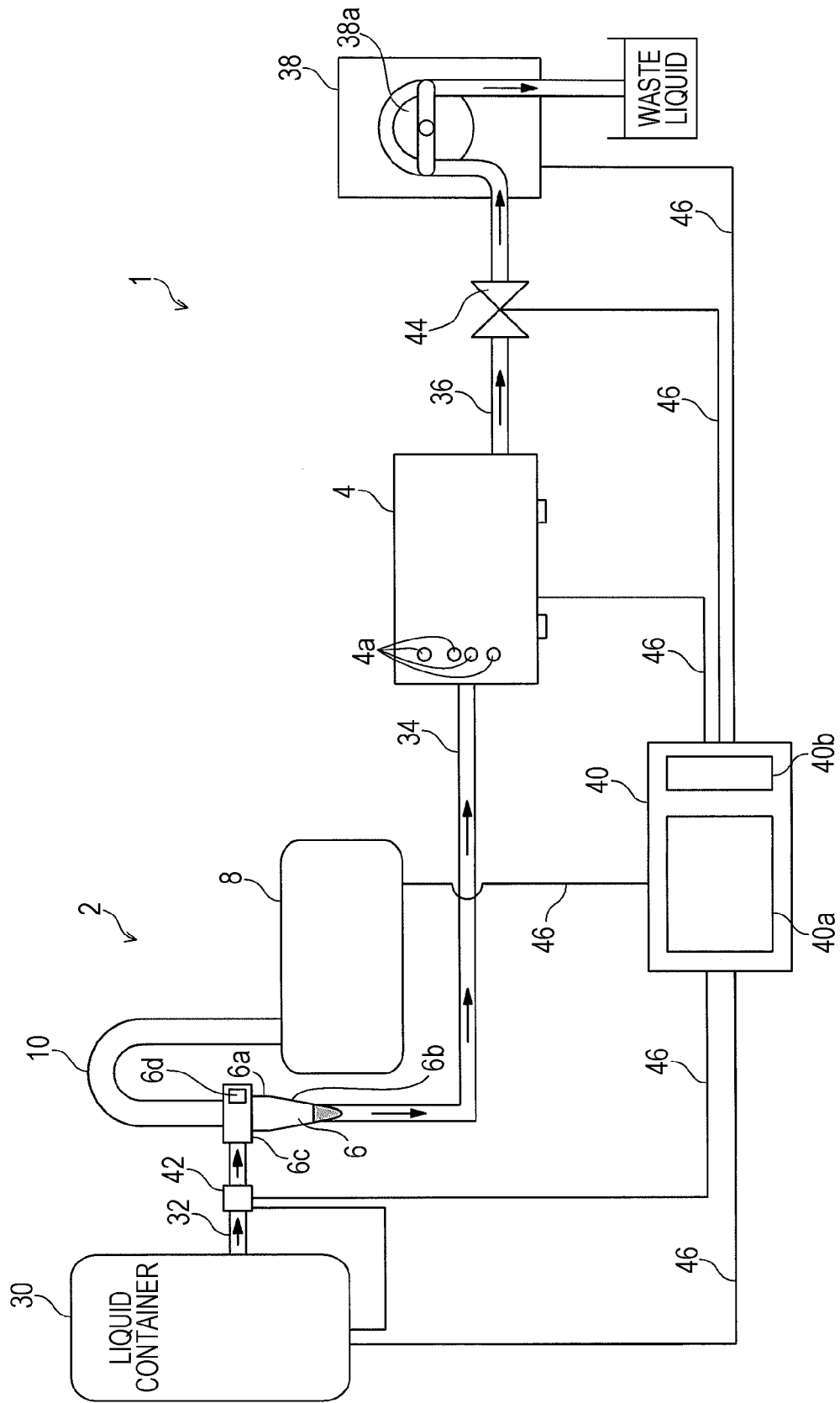
Figure 2:
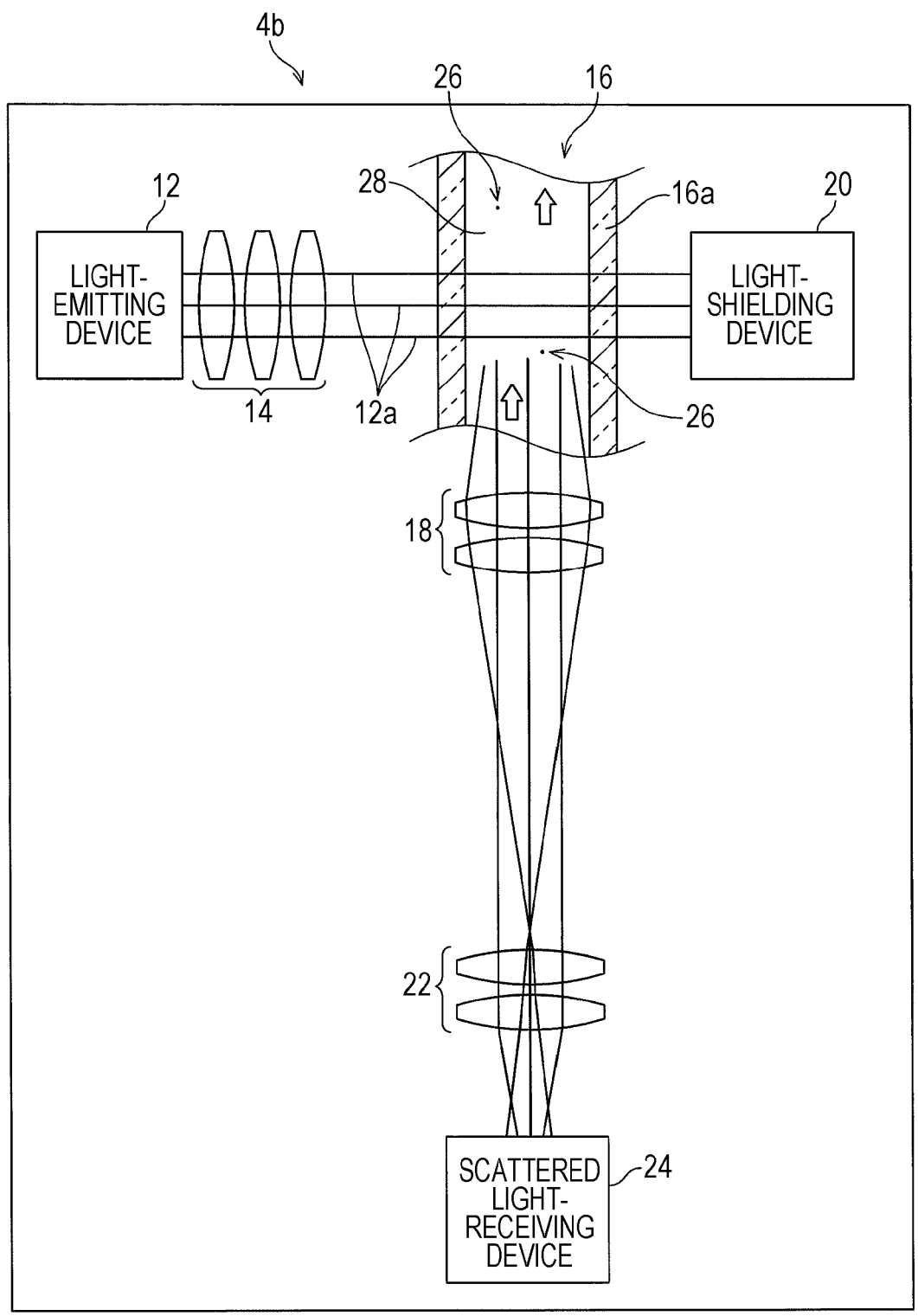

(51) Int. Cl.
*G01N 15/06* (2006.01)
*G01N 15/00* (2006.01)
*G01N 1/22* (2006.01)

(56) References Cited

U.S. PATENT DOCUMENTS

| | | |
|---|---|---|
| 2002/0078826 A1 | 6/2002 | Day |
| 2004/0028561 A1* | 2/2004 | Daugherty et al. ............. 422/99 |
| 2004/0038385 A1* | 2/2004 | Langlois et al. ........... 435/287.1 |
| 2006/0093737 A1* | 5/2006 | Dick et al. ................... 427/180 |
| 2006/0144025 A1 | 7/2006 | Vallayer et al. |
| 2006/0255261 A1* | 11/2006 | Whitehouse et al. ......... 250/288 |
| 2009/0237659 A1 | 9/2009 | Miers |
| 2010/0108910 A1 | 5/2010 | Morrell et al. |
| 2014/0335557 A1* | 11/2014 | Ichijyo et al. .................. 435/34 |

FOREIGN PATENT DOCUMENTS

| | | |
|---|---|---|
| JP | 2002-543975 | 12/2002 |
| JP | 2004-093431 | 3/2004 |
| JP | 3745719 | 2/2006 |
| JP | 2006-508371 | 3/2006 |
| JP | 2009-501907 | 1/2009 |
| JP | 2009-539084 | 11/2009 |
| JP | 4571623 | 10/2010 |
| WO | 00/69568 | 11/2000 |
| WO | 2004/108880 | 12/2004 |
| WO | 2005/001435 | 1/2005 |
| WO | 2007/011854 | 1/2007 |
| WO | 2007/137932 | 12/2007 |

\* cited by examiner

PARTICLE COUNTING SYSTEM

CROSS REFERENCE TO RELATED APPLICATIONS

This application is a U.S. National Phase Application under 35 U.S.C. §371 of International Patent Application PCT/JP2013/003966 filed Jun. 25, 2013 which claims priority to Japanese Patent Application No. 2012-143840 filed Jun. 27, 2012. The International Application was published on Jan. 3, 2014, as International Publication No. WO 2014/002484 A1 under PCT Article 21(2). The entire contents of these applications are hereby incorporated by reference.

TECHNICAL FIELD

The present invention relates to a particle counting system that collects airborne particles in a liquid and measures the number of the particles.

BACKGROUND ART

In general, electronic devices typified by semiconductors, and pharmaceutical products, and the like are manufactured in clean rooms. Such electronic devices, pharmaceutical products, and the like are affected in performance and quality by adhesion of fine particles and microorganisms in the process of manufacture. It is thus preferred that the clean rooms are kept in clean and sterile as much as possible.

Therefore, there have been conventionally used procedures for monitoring the clean condition of a clean room by measuring particles floating in the clean room with a particle counter.

As for measurement of particles floating in a clean room, there has been known a first prior art using an airborne particle counter (see, for example, JP-T-2009-539084: Patent Literature 1). The first prior art is characterized in that an airborne particle counter is equipped with a scroll pump and a photomultiplier-tube. This makes it possible to measure the number of particles in the air at the maximum flow rate of 100 L/min.

There also has been known a second prior art for collecting particles in the air by a collector prior to measurement of the particles by a particle counter (see, for example, Japanese Patent No. 4571623: Patent Literature 2). According to this prior art, a liquid is poured into the container of the collector, the air is sucked into the collector (container), and particles contained in the sucked air are introduced into the liquid by centrifugation.

According to the second prior art, the air can be sucked within the range of flow rates of 200 to 400 L/min., and besides particles in the sucked air can be collected into a liquid of 10 mL.

Besides the second prior art, there has been known a third prior art for collecting airborne particles in a liquid and measuring the number of particles (see, for example, Japanese Patent No. 3745719: Patent Literature 3). According to this prior art, water is reserved in a microorganism analyzer, and the (sucked) air is passed through the water to mix microorganisms and fine particles in the air with the water. Then, the water mixed with the microorganisms and fine particles is irradiated with a laser beam to measure the microorganisms with utilizing their autofluorescence phenomenon.

In recent years, there has been demand for a measurement technique as described below from the viewpoint of more efficiently monitoring the clean condition of a clean room. Specifically, there has been demand for a technique of collecting samples (air) as many as possible in a short time and measuring the number of particles contained in the collected samples in real time. In the first to third prior arts described above, it is simulated that particle measurement is performed at appropriate times at a place as a target of measurement. Accordingly, these prior arts are not suitable for use in automatic measurement of particles at a measurement place for a long period of time.

From the viewpoint of collecting and measuring a large number of samples, the first to third prior arts described above have problems described below.

Specifically, in the first prior art for an airborne particle counter, the more the measurable flow rate of air is increased, the longer the measurement time is taken. In addition, with an increase in flow rate of the air, the inner diameter of a flow cell becomes larger corresponding to the flow rate. This requires expansion of a region for detection of particles. Thus, the range of laser irradiation needs to be expanded. In this case, expanding the range of laser irradiation leads to decrease in the energy density of laser beam. This causes a problem of deteriorated detection sensitivity.

As a countermeasure for the above problems, maintaining the energy density of the laser beam is necessary in order to maintain the sensitivity of detection by increasing the flow rate of the air as well as the flow velocity in the flow cell. In this case, a high-power laser beam source corresponding to the range of irradiation mentioned above is needed. Alternatively, a high-sensitivity light receiving element is needed. However, the use of the high-power laser beam source or the high-sensitivity light receiving element results in cost increase.

As described above, it is extremely difficult to use an airborne particle counter to collect a large number of samples and maintain high detection sensitivity for the particle diameter. If an attempt is made to harmonize collection of a large number of samples with maintenance of high detection sensitivity, the degree of technical difficulty becomes high. Therefore, the first prior art is not suitable for use in collecting a large number of samples and automatically measuring the number of particles at a measurement place for a long period of time.

Meanwhile, according to the method for measuring the number of particles collected in a liquid, the amount (flow rate) of air sucked can be raised without increasing the amount of the liquid as a sample.

The second prior art is thus suited to collecting a large number of samples. However, on measurement of samples with the particle counter, the operator needs to remove the container as a collector and set the container in the particle counter. Thus, the second prior art is not suitable for use in so-called constant monitoring by which changes in the number of particles are monitored for a long time (for example, 24 hours).

According to the third prior art, the state of the air in batches can be measured at a certain time. However, the third prior art does not allow measurement of chronological changes in the number of particles. Therefore, the third prior art is not suitable for use in constant monitoring as with the second prior art.

Under such circumstances as described above, there has been demand for a technique suitable for monitoring of clean condition in relation to collection of particles contained in the air and measurement of the number of the particles.

CITATION LIST

Patent Literatures

Patent Literature 1: JP-T-2009-539084
Patent Literature 2: Japanese Patent No. 4571623
Patent Literature 3: Japanese Patent No. 3745719

SUMMARY OF INVENTION

The invention disclosed herein employs the following solution.

A particle counting system is provided as this solution. The particle counting system includes: an airborne particle collector configured to perform a collecting operation to introduce a surrounding air into a container storing a liquid to collect airborne particles in the liquid; a liquid input/output operation executing means configured to execute a series of liquid input/output operations to supply an additional liquid for the collecting operation to the airborne particle collector and discharges the liquid after the collecting operation from the airborne particle collector; and an liquid-borne particle counter configured to measure the number of particles contained in the liquid discharged from the airborne particle collector with the series of liquid input/output operations.

According to the solution, the supply of the liquid to the airborne particle collector and the discharge of the liquid from the airborne particle collector are executed as the liquid input/output operations. That is, the supply and discharge of the liquid can be automatically controlled. Accordingly, the solution is suited to constant monitoring of the clean condition in the clean room, for example. In addition, the liquid discharged from the airborne particle collector is immediately flown into the liquid-borne particle counter. This allows the liquid-borne particle counter to measure the number of airborne particles in real time.

It is preferred that the airborne particle collector collects the airborne particles in the liquid by centrifugation. Thus, the airborne particle collector can collect the particles smaller than 1 μm in the liquid. This makes it possible to improve the efficiency of particle collection as compared to the case of using the method by which to reserve airborne particles sent from a pump in pure water as described in Patent Literature 3, for example.

In addition, the liquid-borne particle collector may be a viable particle counter that measures the number of viable particles out of particles contained in the liquid, for example. In this case, the liquid-borne particle counter can use an autofluorescence phenomenon to detect fluorescence emitted from the viable particles. Thus, the measurement of the number of viable particles floating in the clean room and changes in the number of the viable particles can be monitored.

The liquid input/output operation executing means includes: a liquid container configured to reserve the additional liquid to be supplied to the airborne particle collector; a first flow path configured to flow the liquid from the liquid container toward the airborne particle collector; a second flow path configured to flow the liquid discharged from the airborne particle collector toward the liquid-borne particle counter; a third flow path configured to flow the liquid after measurement of the number of particles by the liquid-borne particle counter; a pump disposed in the third flow path and flows the liquid from the second flow path to the third flow path via the liquid-borne particle counter; and a flow rate control device configured to control the amount of the liquid supplied from the liquid container to the airborne particle collector and the flow rate of the liquid sent from the second flow path to the third flow path via the liquid-borne particle counter by the pump.

In the particle counting system of the solution, the liquid container and the airborne particle collector are connected together by the first flow path. The airborne particle collector and the liquid-borne particle counter are connected together by the second flow path.

In addition, the flow rate control device controls the supply of the liquid from the liquid container to the airborne particle collector and the supply of the liquid from the airborne particle collector to the liquid-borne particle counter.

Accordingly, there is no need for the operator to, upon completion of the collection of the particles by the airborne particle collector, set the collected sample in the liquid-borne particle counter. This allows automatic execution of a series of operations from the collection of the particles to the measurement of the number of the particles. In addition, the liquid-borne particle counter can measure the particles collected by the airborne particle collector.

The pump causes the liquid at a lower flow rate than the flow rate of the air introduced into the container of the airborne particle collector to flow.

Thus, an liquid-borne particle counter that makes measurement at a general flow rate can be used. In addition, the liquid-borne particle counter can measure the number of the particles contained in the liquid at a constant flow rate without dependence on the flow rate of the air sucked by the airborne particle collector. The amount of the liquid sucked by the pump may be controlled with the use of a valve.

In the particle counting system according to the solution, the flow rate control device causes the liquid container to supply the additional liquid while the airborne particle collector performs the collecting operation, and activates the pump to discharge the liquid from the airborne particle collector to the second flow path after the collecting operation.

Specifically, the collection of the particles can be simultaneously executed by the airborne particle collector and the measurement of the particles by the liquid-borne particle counter. Therefore, changes in the number of particles floating in the clean room can be monitored by making continuous measurement for a predetermined time (for example, 24 hours).

In addition, the liquid in which the particles are collected by the airborne particle collector is immediately supplied to the liquid-borne particle counter. This allows the liquid-borne particle counter to measure the tendencies of increase or decrease in the number of the airborne particles in real time.

After completion of the collecting operation by the airborne particle collector, the flow rate control device may discharge the liquid from the airborne particle collector to the second flow path after the collection operation.

Even in this case, the operator does not have to set the sample collected by the airborne particle collector (the liquid containing the particles) in the liquid-borne particle counter. Thus, intermittent measurement such as 30-minute measurement can be performed at intervals of one hour for 24 hours to investigate changes in the number of particles floating in the clean room, for example.

As another mode of the foregoing intermittent measurement, the solution is suited to measuring the number of particles contained in a predetermined amount of air such as 600 L or 1500 L, for example. Also in this case, the operator does not have to set the sample collected by the airborne particle collector in the liquid-borne particle counter. Thus, for example, it is possible to make measurement in a shorter time than the case with the technique described in Patent Literature 1.

In the particle counting system according to the solution, the liquid input/output operation executing means further includes a liquid flow sensor disposed in the first flow path and detecting the amount of the liquid supplied to the airborne particle collector. At this time, the flow rate control device controls the amount of the liquid supplied from the liquid container to the airborne particle collector, based on the amount of the liquid detected by the liquid flow sensor.

By using the liquid flow sensor as described above, the liquid in the airborne particle collector can be maintained in a fixed amount.

According to the invention disclosed herein, particles in the air can be efficiently collected and the number of the particles can be automatically measured. In addition, even when the flow rate of the air sucked per unit time by the airborne particle collector is increased, there is no need to increase the flow rate of the liquid measured by the liquid-borne particle counter accordingly. Therefore, the time for measuring the number of particles in a predetermined amount of air can be shortened, as compared to the case of measuring the number of particles using the airborne particle counter.

In addition, a series of operations from the collection of airborne particles to the measurement of the number of the particles can be automatically performed. Accordingly, the invention is also suited to a monitoring method for constant monitoring of tendencies of increase or decrease in the number of particles.

BRIEF DESCRIPTION OF THE DRAWINGS

FIG. 1 is a schematic view of a configuration of a particle counting system according to an embodiment;

FIG. 2 is a schematic view of a configuration of inside of a particle counting unit;

FIG. 3 is a block diagram illustrating a flow of control by a flow rate control unit according to the embodiment;

FIG. 4 is a flowchart of a process for continuous measurement;

FIG. 5 is a graph representing changes in the number of particles measured by continuous measurement;

FIG. 6 is a flowchart of a process for intermittent measurement; and

FIG. 7 is a graph representing changes in the amount of a liquid in a container main body.

DESCRIPTION OF EMBODIMENTS

Hereinafter, embodiments will be described with reference to the drawings.

[Embodiment]

FIG. 1 is a schematic view of a configuration of a particle counting system 1 according to an embodiment.

The particle counting system 1 illustrated in FIG. 1 is suitably used in a clean room where electronic devices or pharmaceutical products are manufactured, for example.

The particle counting system 1 includes an airborne particle collector 2 (hereinafter, referred to as collector 2) as a structure for collecting particles in the air. The particle counting system 1 also includes an liquid-borne particle counter 4 (hereinafter, referred to as particle counter 4) as a structure for measuring the number of particles collected.

[Airborne Particle Collector]

The collector 2 performs a collecting operation to introduce the surrounding air into a container storing a liquid to collect airborne particles in the liquid. In the embodiment, the collector 2 collects particles in the air in the liquid by centrifugation. The collector 2 has a container main body (container) 6 and a sucker 8. These components are connected to both ends of a U-shaped pipe 10.

The container main body 6 includes a cylindrical main body portion 6*a* and a truncated cone-shaped bottom portion 6*b*. These portions serve as a centrifugal chamber.

A cap-shaped lid portion 6*c* is fitted into the main body portion 6*a*. An upper surface of the lid portion 6*c* is connected to the pipe 10, and an opening 6*d* for sucking external air is formed on a peripheral surface of the lid portion 6*c*.

A liquid (pure water) is reserved in the bottom portion 6*b*. In the embodiment, the amount of the liquid reserved in the container main body 6 (bottom portion 6*b*) is about 10 mL, for example.

The sucker 8 is a device for sucking the air from the container main body 6. The sucker 8 sucks the air from the container main body 6 through the pipe 10. At that time, external air is introduced into the container main body 6 from the opening 6*d* in the lid portion 6*c*. The sucker 8 forms a spiral air flow in the container main body 6 along an inner wall. At that time, particles in the container main body 6 are centrifuged and collected into the liquid. The flow rate of the air introduced by the sucker 8 into the container main body 6 is approximately 300 L/min., for example.

[Liquid-Borne Particle Counter]

The particle counter 4 measures the number of particles contained in the liquid discharged from the collector 2.

A plurality of indicator lamps 4*a* is attached to a surface of a housing of the particle counter 4. The indicator lamps 4*a* indicate the state of the power source (on or off), measurement state, and network connection state, for example.

The particle counter 4 also includes a particle counting unit 4*b* to measure the number of particles that are collected by the collector 2 into the liquid. FIG. 1 does not illustrate the particle counting unit 4*b*.

The particle counting unit 4*b* radiates light to the liquid that flows in a flow cell and contains a subject (particles). The particle counting unit 4*b* detects scattered lights from the subject and counts the number of the detected scattered lights.

The particle counting unit 4*b* can also measure the number of viable particles. In this case, the particle counting unit 4*b* radiates an ultraviolet light to the liquid that flows in a flow cell and contains subjects (viable particles and non-viable particles). The particle counting unit 4*b* separates and extracts autofluorescence lights emitted from the viable particles using a dichroic mirror and an optical filter or the like, and counts the number of the lights.

FIG. 2 is a schematic view of a configuration of inside of the particle counting unit 4*b*.

To detect scattered lights, the particle counting unit 4*b* includes a light-emitting device 12, an irradiation optical lens system 14, a flow cell 16, a first light-collecting optical lens system 18, a light-shielding device 20, a second light-collecting optical lens system 22, and a scattered light-receiving device 24.

[Light-Emitting Device]

The light-emitting device 12 includes, for example, a semiconductor laser diode (including a semiconductor LED element, and hereinafter referred to as laser diode). The laser diode 12 radiates laser beams 12*a* to a liquid (pure water) containing particles.

[Irradiation Optical Lens System]

The irradiation optical lens system 14 includes a plurality of kinds of optical lenses, for example. The optical lenses include a collimator lens, a biconvex lens, and a cylindrical lens, for example. The irradiation optical lens system 14 irradiates the subject with the laser beams 12*a* oscillated from the laser diode 12.

[Flow Cell]

The flow cell 16 includes a hollow square-columnar cylindrical portion 16*a* made from synthesized crystal, sapphire, and the like, for example. The flow cell 16 is structured as to flow a liquid (pure water) 28 containing particles 26 as a subject from the bottom to the up. The laser beams 12a are radiated to a hollow region of the cylindrical portion 16a in which the liquid (pure water) flows, thereby to form a detection region.

These lights are detected by the scattered light-receiving device 24 through the first light-collecting optical lens system 18 and the second light-collecting optical lens system 22. The intensities of the scattered lights, that is, the amounts of the scattered lights depend on the size of the particles 26. The larger the particles are in size, the greater the amounts of the lights become. In addition, when a larger number of laser beams 12a with enhanced laser power are radiated to the flow cell 16, the scattered lights from the particles 26 increase accordingly.

[Light-Shielding Device]

The light-shielding device 20 includes a laser trap (hereinafter, referred to as laser trap 20), for example. The laser trap 20 shields the laser beams 12a that have been oscillated from the laser diode 12 and then passed through the flow cell 16.

[First Light-Collecting Optical Lens System]

The first light-collecting optical lens system 18 includes, for example, a plurality of optical lenses. The first light-collecting optical lens system 18 is positioned at an angle of approximately 90 degrees relative to the traveling direction of the laser beam 12a (optical axis). The first light-collecting optical lens system 18 collects the scattered lights from the particles 26 in the flow cell 16.

It is preferable that the diameters of the lenses are large to collect the lateral scattered lights from the particles 26 as much as possible. The lens diameters are decided depending on the position (distance) of a detection device for detecting the scattered lights from the particles 26.

[Second Light-Collecting Optical Lens System]

The second light-collecting optical lens system 22 includes a plurality of optical lenses, for example. The second light-collecting optical lens system 22 is positionedprovided on the traveling direction (optical axis) of the lights having passed through the first light-collecting optical lens system 18. The second light-collecting optical lens system 22 collects the scattered lights having passed through the first light-collecting optical lens system 18 and forms an image onto an incidence plane of the scattered light-receiving device 24.

[Scattered Light-Receiving Device]

The scattered light-receiving device 24 includes a photo diode or a photomultiplier, for example. The scattered light-receiving device 24 receives the scattered lights from the particles 26 that have passed through the second light-collecting optical lens system 22. The lights received at the scattered light-receiving device 24 are converted into an electric signal according to the light amounts. The electric signal is output from the scattered light-receiving device 24. A counting system, which is not illustrated, measures the number of the particles on the basis of the signal output from the scattered light-receiving device 24.

[Liquid Input/Output Operation Executing Means]

The particle counting system 1 according to the embodiment illustrated in FIG. 1 also includes a liquid input/output operation executing means. The liquid input/output operation executing means executes a series of liquid input/output operations to supply an additional liquid for collecting operation to the collector 2 and discharge the liquid after the collecting operation from the collector 2.

As a configuration for realizing this, the liquid input/output operation executing means has a liquid container 30, a pipe 32 as a first flow path, a pipe 34 as a second flow path, a tube 36 as a third flow path, and a pump 38. The liquid input/output operation executing means also has a flow rate control device 40.

[Liquid Container]

The liquid container 30 reserves an additional liquid to be supplied to the collector 2. The liquid container 30 has a predetermined amount of liquid reserved therein in advance. An appropriate amount of the liquid reserved is supplied from the liquid container 30 to the collector 2. The amount of the liquid reserved in the liquid container 30 can be freely set by the operator according to the flow rate of the liquid flowing in the particle counter 4 and the time required for measurement of the number of the particles, for example.

In the embodiment, the liquid container 30 causes the liquid to flow toward the collector 2 by applying a pressure, for example. Alternatively, the liquid container 30 may cause the liquid to flow by the use of a gravity force.

[First Flow Path]

The pipe 32 connects the liquid container 30 to the collector 2 to flow the liquid from the liquid container 30 to the collector 2.

A liquid flow sensor 42 is attached to the pipe 32. The liquid flow sensor 42 detects the amount of the liquid supplied to the collector 2. The flow rate control device 40 controls the amount of the liquid supplied from the liquid container 30 such that the liquid supplied to the collector 2 reaches a predetermined amount (10 mL) according to a signal output from the liquid flow sensor 42, for example.

[Second Flow Path]

The pipe 34 connects the collector 2 to the particle counter 4 to flow the liquid discharged from the collector 2 toward the particle counter 4.

[Third Flow Path]

The tube 36 connects the particle counter 4 to the pump 38 to flow the liquid after the measurement of the number of the particles by the particle counter.

[Pump]

The pump 38 causes the liquid to flow from the pipe 34 toward the tube 36 via the particle counter 4. The pump 38 has a roller 38a. The tube 36 is wound around the roller 38a. The pump 38 will be hereinafter referred to as roller pump 38. In the embodiment, the pump is not limited to the roller pump 38. Instead of the roller pump 38, another kind of liquid sucking pump may be used as long as a desired condition is met.

The roller pump 38 rotates the roller 38a. The tube 36 is pressed with the rotation of the roller 38a to flow the liquid in the tube 36. When the roller 38a stops rotation, the liquid in the tube 36 and the liquid in the pipe 34 also stop flowing.

The liquid in the container main body 6 is sent to the particle counter 4 through the pipe 34. The liquid in the container main body 6 is also sent from the particle counter 4 to the roller pump 38 through the tube 36. Then, the liquid in the container main body 6 is discharged as a waste liquid to the outside.

The tube 36 may be provided with a valve 44 to adjust the flow rate of the liquid discharged from the container main body 6. However, the valve 44 may not be provided as far as the roller pump 38 can flow the liquid at a predetermined flow rate (for example, 10 mL/min.). In addition, the pump 38 can be built in the particle counter 4.

[Flow Rate Control Device]

The flow rate control device 40 (hereinafter, referred to as controller 40) controls the amount of the liquid supplied from the liquid container 30 to the collector 2 and the flow rate of the liquid from the pipe 34 to the tube 36 via the particle counter 4 caused by the roller pump 38.

In the particle counting system 1 according to the embodiment, the liquid container 30, the collector 2, the particle counter 4, and the roller pump 38 are electrically connected to the controller 40 via a network cable 46. In addition, the liquid flow sensor 42 and the valve 44 are connected to the controller 40 via the network cable 46.

The controller 40 has a display 40*a* mounted therein to display the measurement status to the operator. The controller 40 also has an operation panel 40*b* mounted therein to set conditions for particle measurement by the particle counter 4.

If a preset value is exceeded, the controller 40 issues a warning. This makes it possible to inform the operator of occurrence of an abnormality in the clean condition of the clean room, for example.

In the embodiment, the controller 40 also includes a flow rate control unit 40*c*. Incidentally, FIG. 1 does not illustrate the flow rate control unit 4*c*.

[Flow Rate Control by the Controller]

Figure 3:
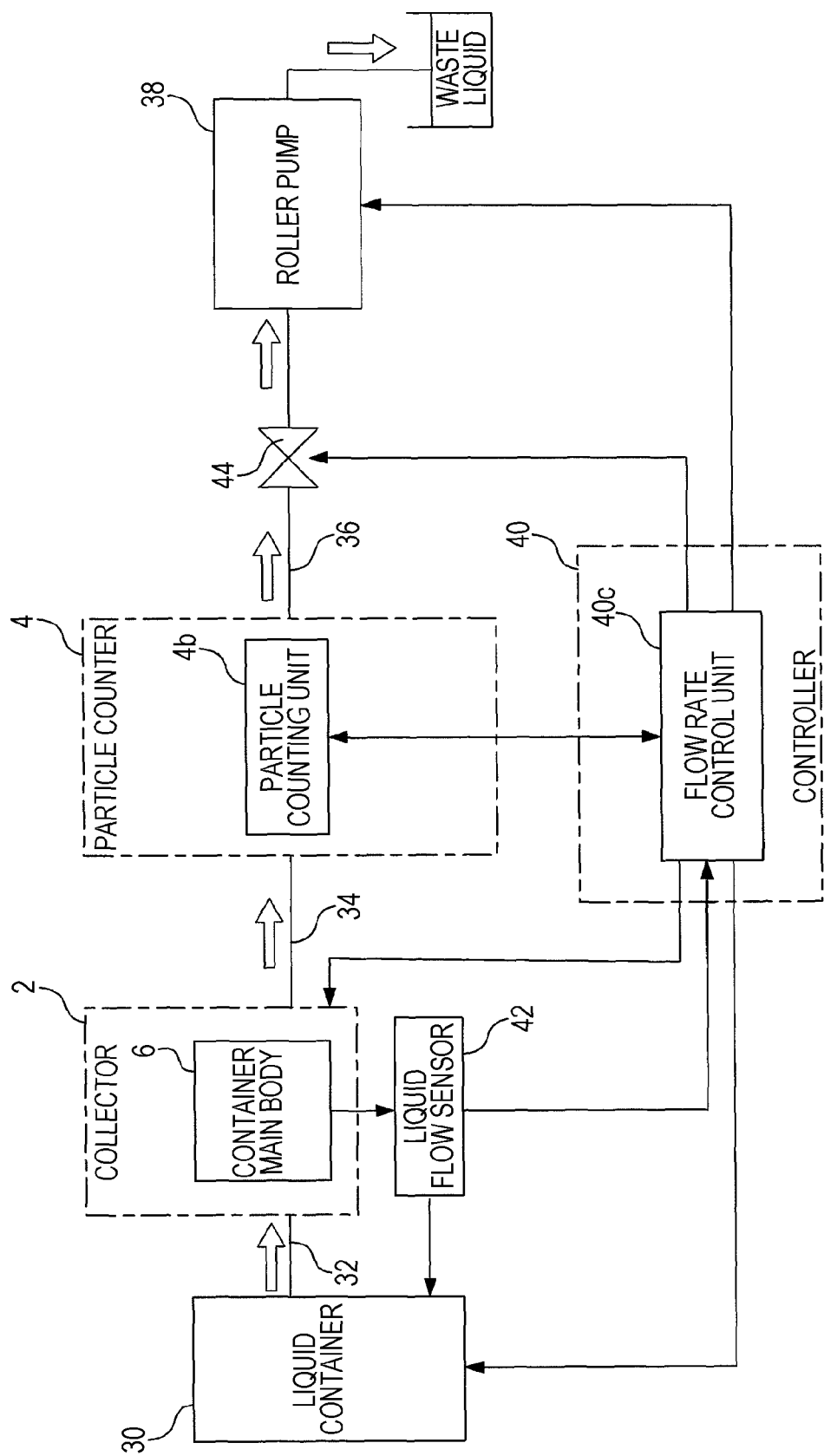

FIG. 3 is a block diagram illustrating a flow of control by the flow rate control unit 40*c* according to the embodiment. Open arrows in FIG. 3 indicate a flow of the liquid. Solid arrows in FIG. 3 indicate a flow of control by the flow rate control unit 40*c*.

[Supply of the Liquid to the Airborne Particle Collector]

The flow rate control unit 40*c* outputs a signal to the liquid container 30 to instruct for starting of liquid supply. Upon receipt of the signal, the liquid container 30 starts supply of the liquid to the container main body 6.

At this time, the liquid container 30 can supply the liquid to the container main body 6 by the use of a method for applying a pressure to the liquid by a pressuring means (not illustrated). The liquid container 30 can also supply the liquid to the container main body 6 by the use of a method for flowing the liquid by a gravity force or the like.

The liquid container 30 also supplies a predetermined amount of liquid (for example, 10 mL) to the container main body 6 according to the input signal, or continuously supplies the liquid to the container main body 6 at a predetermined flow rate (for example, 10 mL/min.).

The liquid flow sensor 42 is arranged in the pipe 32. An electric signal output from the liquid flow sensor 42 is output to the flow rate control unit 40*c*.

In this case, the flow rate control unit 40*c* may control the amount of the liquid supplied from the liquid container 30 to the container main body 6 according to the input electric signal. The liquid flow sensor 42 may output the foregoing signal to the liquid container 30. In this case, the liquid container 30 controls the amount of the liquid supplied according to the input electric signal.

[Collection of Particles by the Airborne Particle Collector]

The flow rate control unit 40*c* outputs a signal to the collector 2 to instruct for starting suction of the air. Upon receipt of the signal, the collector 2 sucks the air. Then, the collector 2 collects particles contained in the sucked air into the liquid supplied from the liquid container 30.

Specifically, the sucker 8 is first activated to introduce the surrounding air into the container main body 6. At this time, the sucker 8 sucks the air at a flow rate of 300 L/min., for example.

The air introduced into the container main body 6 rotates and flows within the container main body 6. In such a manner, the particles contained in the air are collected into the liquid by centrifugation.

[Supply of the Liquid to the Liquid-Borne Particle Counter]

The flow rate control unit 40*c* outputs a signal to the roller pump 38 to instruct for activating. Upon receipt of the signal, the roller pump 38 rotates the roller 38*a*. With the rotation of the roller 38*a*, the liquid in the container main body 6 is sucked. The sucked liquid flows to the particle counter 4 through the pipe 34. In addition, the liquid in which the number of particles is measured by the particle counter 4 flows to the roller pump 38 through the tube 36, and then is discharged as a waste liquid to the outside. At this time, the flow rate of the liquid flowing through the pipe 34 and the tube 36 is 10 mL/min., for example.

In such a manner, activating the roller pump 38 allows the liquid in the collector 2 to flow toward the particle counter 4.

[Measurement of Particles by the Liquid-Borne Particle Counter]

The flow rate control unit 40*c* outputs a signal to the particle counter 4 (particle counting unit 4*b*) to instruct for starting measurement of the number of particles.

Upon receipt of the signal, the particle counter 4 measures the number of particles contained in the liquid having reached through the pipe 34. There is generally known a method by which, in the case where the liquid contains air bubbles, the air bubbles and the particles are distinguished. Thus, the particle counter 4 may execute the foregoing discrimination method on measurement of the particles.

The number of the particles measured is displayed on the display 40*a* of the controller 40, for example. The controller 40 also saves chronological data in the storage medium of the controller 40 and displays on the display 40*a* a graph representing changes in the number of the particles. The controller 40 may be connected to a PC (personal computer). In this case, a graph indicating the number of the particles and changes in the number of the particles measured by the particle counter 4 may be displayed on the display of the PC.

The manager of the clean room can monitor the number of the particles and the chronological changes in the number of the particles displayed on the display 40*a* to recognize the clean condition of the clean room.

In addition, as described above, if a preset value is exceeded, the controller 40 can issue a warning to inform this event to the operator.

The flow rate control unit 40*c* outputs a signal to the roller pump 38 in operation to instruct for stopping. Upon receipt of the signal, the roller pump 38 stops the rotation of the roller 38*a*. Accordingly, the discharge of the liquid from the container main body 6 is stopped.

As described above, according to the particle counting system 1 of the embodiment, the controller 40 controls supply of the liquid from the liquid container 30 and discharge of the liquid from the collector 2 (container main body 6).

This eliminates the need for the operator to, after completion of the collection of the particles by the collector 2, set the collected sample into the particle counter 4. The collection of particles to the measurement of the number of the particles can be automatically conducted.

Therefore, simply by setting measurement conditions to the controller 40, the operator (manager) can measure the number of the particles for consecutive 24 hours or measure the number of the particles intermittently at predetermined time intervals (for example, every one hour).

In the embodiment, a method is employed by which particles in the air are collected into a liquid (approximately 10 mL) in the container main body 6. Therefore, for example, even if the air is sucked at a flow rate of either 100 L/min. or 300 L/min., the particles contained in the air for each flow rate are concentrated in the liquid of 10 mL.

Accordingly, the particle counter 4 can make measurement on the liquid of 10 mL that is sufficiently smaller in amount than the sucked air. Therefore, the measurement time can be significantly shortened as compared to the case where the air is directly introduced into the particle counter 4 for measurement of the particles. In addition, an liquid-borne particle counter, which allows measurement at a general flow rate, can be used. There is also no need to adjust power of laser beams from the light-emitting device 12, according to the amount of the air sucked. Further, according to the particle counting system 1 of the embodiment, the number of particles can be measured without dependence on the amount of the air sucked. This makes it possible to maintain the sensitivity to the particle diameter.

[Measurement Process]

Next, a method for measurement of particles in the particle counting system 1 of the embodiment will be described.

In the particle counting system 1, the collection by the collector 2 and the measurement by the particle counter 4 can be continuously or intermittently executed. First, the method for continuous collection and measurement will be described below.

[Continuous Measurement]

Figure 4:
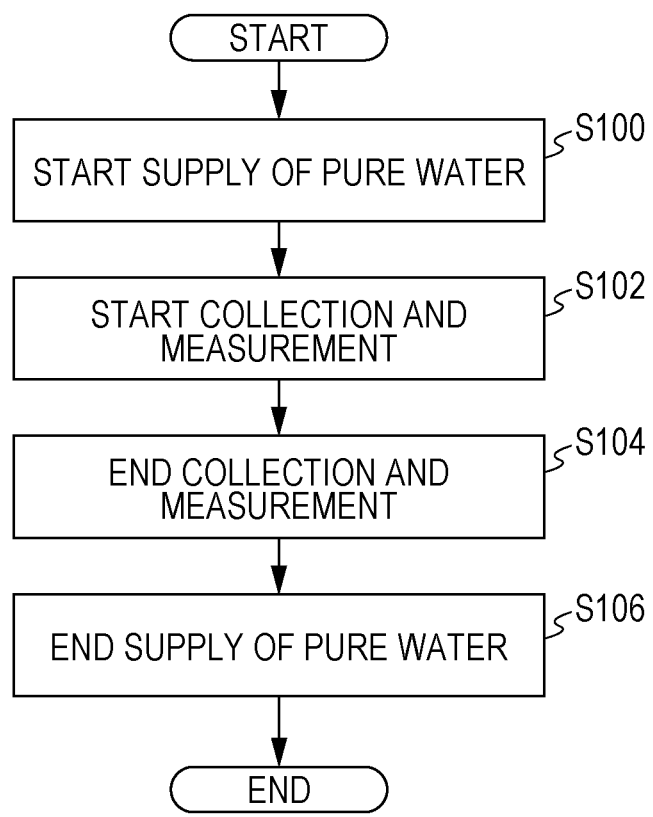

FIG. 4 is a flowchart of a process for the continuous measurement. The method for continuous execution described above refers to a method for executing simultaneously collection of particles by the collector 2 and measurement of the number of the particles by the particle counter 4 to make continuous measurement for a predetermined time (for example, 24 hours). Hereinafter, this method will be referred to as "continuous measurement."

Step S100: The flow rate control unit 40c causes the liquid container 30 to start supply of pure water (liquid).

Next, the flow rate control unit 40c opens the valve 44 and activates the roller pump 38. The roller pump 38 rotates the roller 38a to flow the liquid supplied to the container main body 6 from the pipe 34 toward the tube 36. Then, the insides of the pipe 34, the particle counter 4, and the tube 36 are filled with the pure water.

At this time, according to an output signal from the liquid flow sensor 42, the controller 40 causes the liquid container 30 to control the amount of the liquid supplied so that the liquid in the container main body 6 of the collector 2 can be retained in a predetermined amount (10 mL).

The roller pump 38 flows the liquid flowing through the pipe 34, the particle counter 4, and the tube 36 at a flow rate of 10 mL/min., for example. The amount of the liquid sucked by the roller pump 38 (10 mL/min.) is adjusted by the valve 44. The particle counting system 1 may not be configured to include the valve 44 as far as the flow rate can be sufficiently adjusted by the pump 38.

Instead of using the liquid flow sensor 42, the controller 40 may memorize in advance the time between the instant at which the pump 38 is activated and the instant at which the insides of the pipe 34, the particle counter 4, and the tube 36 are filled with the pure water (liquid distribution time). This liquid distribution time can be set based on the total length of the pipe 34 and the tube 36 and the amount sucked by the roller pump 38, for example.

Step S102: The flow rate control unit 40c causes the collector 2 to start suction of the air. The flow rate control unit 40c also causes the particle counter 4 to start measurement of the particles.

The sucker 8 of the collector 2 sucks the air in the clean room at a flow rate of 300 L/min., for example. The particle counter 4 radiates a laser beam to the pure water flowing at a flow rate of 10 mL/min. to detect scattered lights from the particles, and measures the number of the particles according to the scattered lights detected.

Step S104: When a predetermined time (for example, 24 hours) has elapsed since the starting of the suction of the air and the measurement of the particles, the flow rate control unit 40c causes the collector 2 and the particle counter 4 to end the suction of the air and the measurement of the particles, respectively. Alternatively, the operator may manually end the measurements by the collector 2 and the particle counter 4.

Step S106: Next, the flow rate control unit 40c causes the liquid container 30 to stop supply of the pure water. However, the roller pump 38 continues to operate. The roller pump 38 discharges the pure water as a waste water from the container main body 6, the pipe 34, the particle counter 4, the tube 36, and the roller pump 38 to the outside.

Finally, the flow rate control unit 40c closes the valve 44 and stops the roller pump 38 to terminate this process.

The particle counting system 1 of the embodiment may include a device for automatically supplying pure water to the liquid container 30. With such a configuration, there is no concern that the pure water in the liquid container 30 becomes depleted. Thus, this configuration is suited to constant monitoring.

Figure 5:
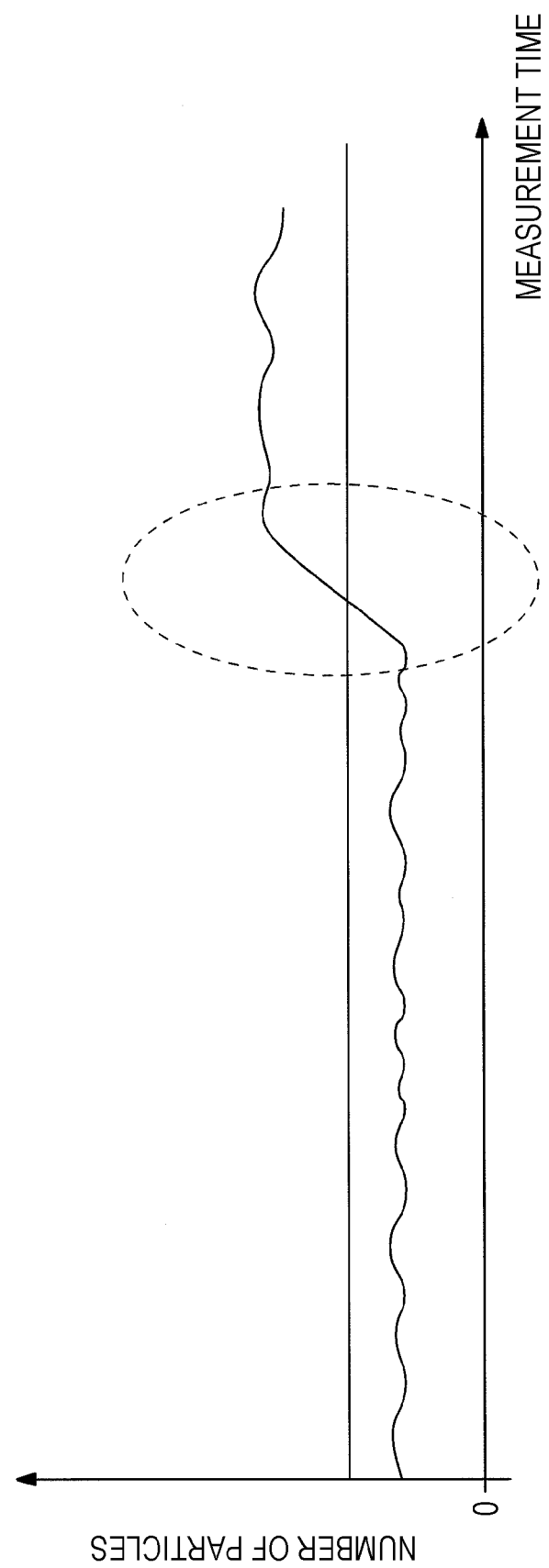

FIG. 5 is a graph representing changes in the number of particles measured by continuous measurement.

The status of measurement of the particles by continuous measurement is displayed on the display 40a of the controller 40 or the display of a PC connected to the controller 40 but not illustrated. If a preset value is exceeded, the controller 40 can issue a warning to inform this to the operator.

In the graph of FIG. 5, the vertical axis indicates the number of particles contained in the liquid flowing at a predetermined flow rate, and the lateral axis indicates the measurement time. The lateral line in the graph indicates the reference value of the number of particles.

For example, a clean air is supplied in the clean room. The clean room is kept in almost a clean condition. Accordingly, the number of the particles measured by the particle counter 4 is almost constant.

However, in the section surrounded by a dotted line of FIG. 5, the number of scattered lights detected, that is, the number of the particles sharply increases, and as a result, the number of the particles exceeds the reference value. In this case, the manager can recognize that the degree of cleanness in the clean room is lowered.

As described above, the continuous measurement allows simultaneous execution of the collection of the particles by the collector 2 and the measurement of the particles by the particle counter 4. Therefore, the continuous measurement makes it possible to monitor changes in the number of the particles floating in the clean room.

The liquid after the collection of the particles by the collector 2 is immediately supplied to the particle counter 4. This allows the particle counter 4 to measure the number of particles in the air in real time. The particle counting system 1 of the embodiment may include a device for automatically supplying pure water to the liquid container 30. With such a configuration, there is no concern that the pure water in the liquid container 30 becomes depleted. Thus, this configuration is suited to constant monitoring.

According to the foregoing measurement method, the liquid flow sensor 42 is used as an example. However, continuous measurement is allowed without the use of the liquid flow sensor 42.

Specifically, the liquid container 30 supplies the liquid at a constant flow rate (10 mL/min.). Thus, the roller pump 38 also flows the liquid at a constant flow rate (10 mL/min.).

Therefore, by setting in advance to the controller 40, according to the foregoing flow rate, (1) the time required to fill the pure water into the pipe 32, (2) the time required for the pure water in the container main body 6 to reach a predetermined amount, and (3) the time required to fill the pure water into the pipe 34 and the tube 36, the controller 40 can activate the liquid container 30, the collector 2, the particle counter 4, and the pump 38 at predetermined timings.

[Intermittent Measurement]

Next, the method for executing intermittently the collection and measurement of particles will be described.

Figure 6:
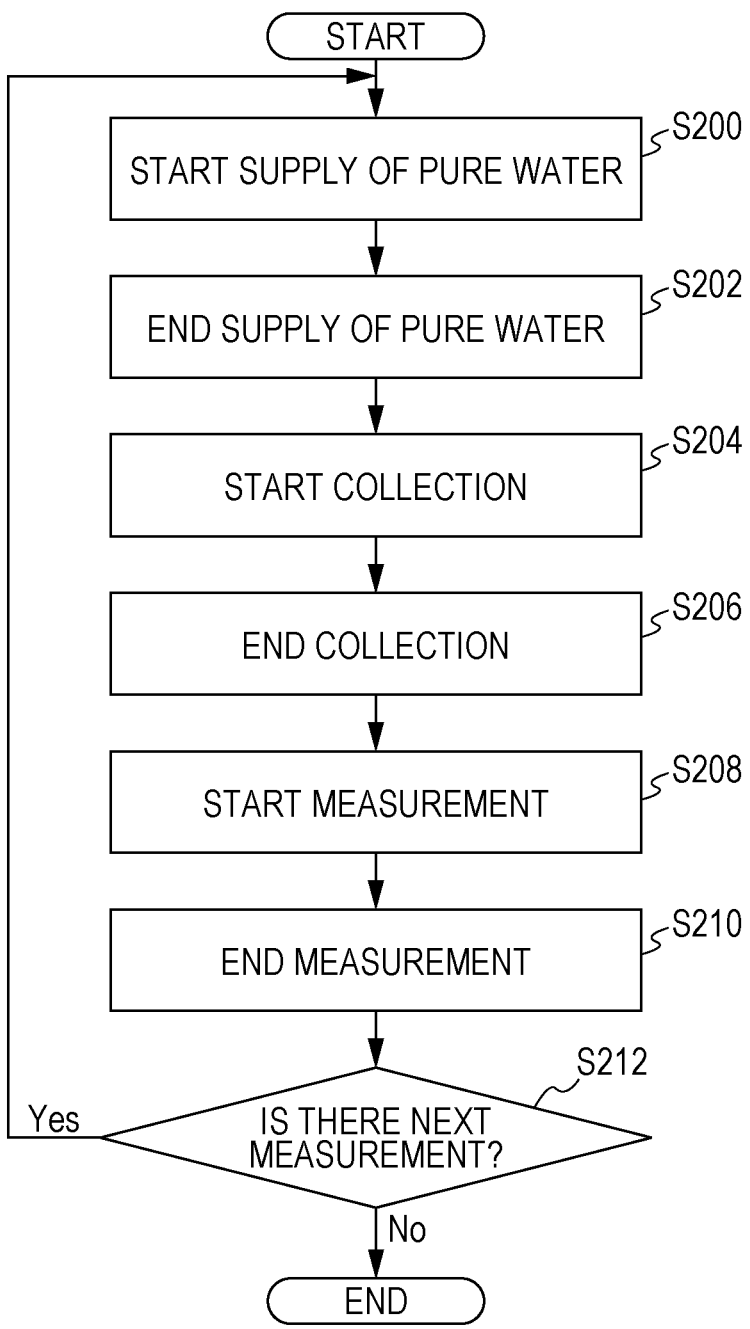

FIG. 6 is a flowchart of a process for intermittent measurement. The foregoing method for intermittent execution refers to a method for executing intermittently the following cycle at predetermined time intervals. Specifically, a process from collection of the particle to completion of the measurement is executed in the one cycle. Hereinafter, the method for executing the cycle intermittently and repeatedly will be referred to as "intermittent measurement". The intermittent measurement also includes the case where the measurement is completed only in one cycle (single measurement).

Step S200: The flow rate control unit 40c causes the liquid container 30 to start supply of the pure water (liquid).

Next, the flow rate control unit 40c opens the valve 44 and activates the roller pump 38. The roller pump 38 rotates the roller 38a to flow the liquid supplied to the container main body 6 from the pipe 34 toward the particle counter 4 and the tube 36. Then, the insides of the pipe 34, the particle counter 4, and the tube 36 are filled with the pure water.

At this time, the liquid flow sensor 42 causes the liquid container 30 to control the amount of the liquid supplied so that the liquid in the container main body 6 of the collector 2 can be maintained in a predetermined amount (10 mL).

The roller pump 38 flows the liquid in the pipe 34, the particle counter 4, and the tube 36 at a flow rate of 10 mL/min., for example. The amount of the liquid sucked by the pump 38 (10 mL/min.) is adjusted by the valve 44. The particle counting system 1 may not include the valve 44 as far as the roller pump 38 can sufficiently control the flow rate.

Step S202: Next, the flow rate control unit 40c causes the liquid container 30 to stop supply of the pure water. At that time, the flow rate control unit 40c closes the valve 44 and stops the roller pump 38.

At this time, the container main body 6 reserves 10 mL of the pure water. The pipe 34, the particle counter 4, and the pipe 40 are also filled with the pure water.

Step S204: The flow rate control unit 40c causes the collector 2 to start suction of the air. The collector 2 sucks the air at a flow rate of 300 L/min., and collects particles contained in the air into the pure water by centrifugation.

Step S206: Upon lapse of a predetermined period of time, the flow rate control unit 40c causes the collector 2 to stop the suction of the air.

Step S208: Next, the flow rate control unit 40c causes the particle counter 4 to start measurement of the particles.

Specifically, the flow rate control unit 40c opens the valve 44 and activates the roller pump 38. Accordingly, the pure water in the container main body 6 flows toward the particle counter 4 through the pipe 34. The particle counter 4 performs the measurement until the liquid in the container main body 6 and the pipe 34 is all discharged to the outside. That is, the time required until the liquid is all discharged to the outside constitutes the measurement time.

The pipe 34 and the particle counter 4 are filled in advance with the pure water at step S200. Accordingly, the time (interval) required between the instant at which the collection of the particles by the collector 2 is terminated and the instant at which the particle counter 4 starts the measurement may be set based on the time required until the pure water filled in advance in the pipe 34 is all flown to the tube 36.

Step S210: Upon lapse of the measurement time, the flow rate control unit 40c causes the particle counter 4 to stop the measurement.

The measurement time is set to the controller 40 based on the amount of liquid sucked by the roller pump 38 (10 mL/min.). Alternatively, the measurement time may be set in the particle counter 4.

The flow rate control unit 40c closes the valve 44 and stops the roller pump 38.

Step S212: The flow rate control unit 40c determines whether the next measurement is reserved or not. When the next measurement is reserved (Yes), step S200 is executed when the reservation time is reached.

Meanwhile, when the next measurement is not reserved (No), the flow rate control unit 40c terminates this process. At termination of this process, the flow rate control unit 40c may output a signal to the particle counter 4 for instructing power-off. Upon receipt of the signal, the particle counter 4 powers off.

Figure 7:
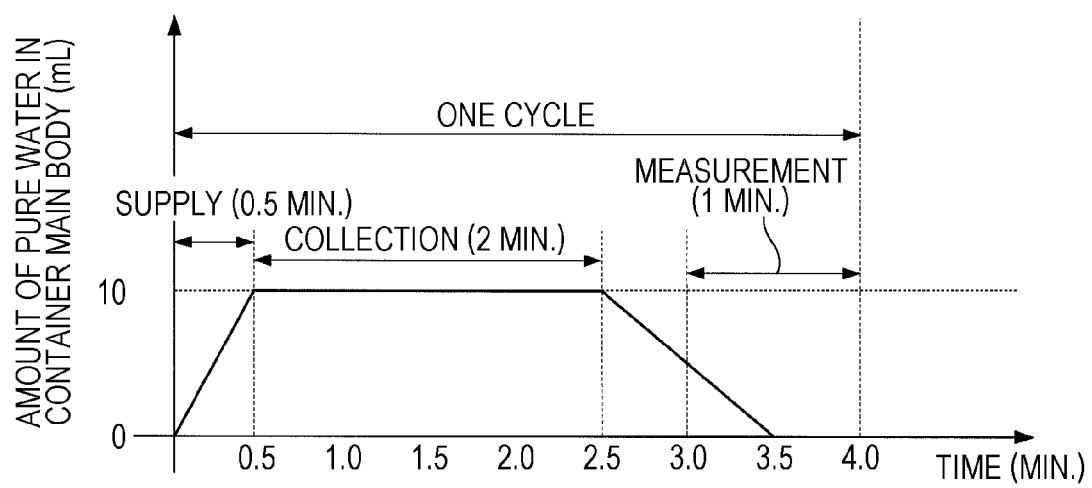

FIG. 7 is a graph representing changes in the amount of the liquid in the container main body 6. The graph indicates changes in the amount of the liquid in the container main body 6 in one cycle.

In FIG. 7, the vertical axis indicates the amount of the pure water in the container main body 6, and the lateral axis indicates the time elapsed since the liquid container 30 has started the supply of the pure water.

The pure water in the container main body 6 reaches a predetermined amount (10 mL) in 30 seconds (0.5 minute) since the liquid container 30 has started the supply of the pure water.

Next, the collector 2 collects particles in the air. At the intermittent measurement, during which the collector 2 collects the particles, the liquid container 30 does not supply the pure water. Accordingly, the amount of the pure water in the container main body 6 is kept almost constant.

It is here assumed that the time required for the collector 2 to collect the particles is two minutes (the air of 600 L). Upon termination of the collection of the particles by the collector 2, the particle counter 4 starts the measurement of the particles. At this time, the roller pump 38 is activated to flow the pure water in the container main body 6 toward the particle counter 4 through the pipe 34.

This example takes into account the time required for the pure water containing the particles to reach the particle counter 4 from the collector 2. Therefore, the particle counter 4 starts the measurement 30 seconds after (0.5 minute after) since the collection of the particles by the collector 2 is terminated.

In such a manner, also for the intermittent measurement, there is no need for the operator to set the sample collected by the collector 2 (liquid containing the particles) in the particle counter 4. Thus, intermittent measurement such as 30-minute measurement at intervals of one hour for 24 hours can be performed to investigate changes in the number of particles floating in the clean room, for example.

As described above, according to the particle counting system 1 of the embodiment, particles in the air can be efficiently collected and the particles can be rapidly measured.

For example, in the case of using an airborne particle counter configured to measure directly the number of airborne particles, the measurement time becomes longer according to the flow rate of the air sucked.

In contrast, according to the particle counting system 1 of the embodiment, as apparent from the graph illustrated in FIG. 7, the time required for executing one cycle from the starting of the supply of a liquid to the completion of the measurement of the number of particles is approximately four minutes per air of 600 L. In the particle counting system 1 of the embodiment, as the collection time in one cycle is increased, the time efficiency of measurement of the number of the particles becomes higher.

For example, the flow rate of the liquid flowing through the particle counter 4 is 10 mL/min. even when the amount of the air is increased. Therefore, rapid measurement can be performed without dependence on the flow rate of the air sucked by the collector 2.

According to the particle counting system 1 of the embodiment, the particles contained in the air sucked by the collector 2 are introduced into the liquid by centrifugation. Accordingly, as compared to the method by which particles in the air sent from the pump are reserved in the pure water, the collector 2 can collect even particles smaller than 1 μm into the liquid.

The invention disclosed herein is not limited to the embodiment described above. The invention can be carried out in various modified embodiments. For example, the particle counter 4 may use a autofluorescence phenomenon to measure the number of viable particles out of the particles contained in the liquid. In this case, even if the liquid contains air bubbles, there is a difference in wavelength between scattered lights reflected from the air bubbles and fluorescence emitted from the viable particles, and thus the particle counter 4 can distinguish these lights. That is, the particle counter 4 can detect only the fluorescence. The particle counter 4 can thus measure the number of the viable particles.

The controller 40 of the embodiment is described above as a device separated from the particle counter 4. However, the controller 40 may be integrated with the particle counter 4.

In the intermittent measurement in the particle counting system 1 of the embodiment, the number of particles in the air introduced by the particle counter 4 can be measured. With regard to the intermittent measurement, assuming that the efficiency of particle collection is not 100%, the particle counter 4 may be provided with a means for correcting measurement results based on the efficiency of particle collection determined in advance by experiments or the like.

LIST OF REFERENCE NUMERALS

1 Particle counting system
2 Collector (airborne particle collector)
4 Particle counter (liquid-borne particle counter)
30 Liquid container
32 Pipe (first flow path)
34 Pipe (second flow path)
26 Tube (third flow path)
38 Roller pump (pump)
40 Controller (flow rate control device)
40c Flow rate control unit
42 Liquid flow sensor
44 Valve

The invention claimed is:
1. A particle counting system comprising:
an airborne particle collector performing a collecting operation to introduce a surrounding air into a container storing a liquid to collect airborne particles in the liquid;
a liquid supply and discharge system executing a series of liquid supply and discharge operations to supply an additional liquid for the collecting operation to the airborne particle collector and discharges the liquid after the collecting operation from the airborne particle collector, and
a liquid-borne particle counter measuring the number of particles contained in the liquid discharged from the airborne particle collector during the series of liquid supply and discharge operations,
wherein the liquid supply and discharge system comprises:
a liquid container reserving the additional liquid to be supplied to the airborne particle collector;
a first flow path flowing the liquid from the liquid container toward the airborne particle collector;
a second flow path flowing the liquid discharged from the airborne particle collector toward the liquid-borne particle counter;
a third flow path flowing the liquid after measurement of the number of particles by the liquid-borne particle counter;
a pump disposed in the third flow path and flows the liquid from the second flow path to the third flow path via the liquid-borne particle counter; and
a flow rate control device controlling the amount of the liquid supplied from the liquid container to the airborne particle collector and the flow rate of the liquid sent from the second flow path to the third flow path via the liquid-borne particle counter by the pump.

2. The particle counting system according to 1, wherein the pump causes the liquid at a lower flow rate than the flow rate of the air introduced into the container of the airborne particle collector to flow.

3. The particle counting system according to claim 2, wherein
the flow rate control device causes the liquid container to supply the additional liquid while the airborne particle collector performs the collecting operation, and activates the pump to discharge the liquid from the airborne particle collector to the second flow path after the collecting operation.

4. The particle counting system according to claim 3, wherein
the liquid supply and discharge system further includes a liquid flow sensor disposed in the first flow path and detecting the amount of the liquid supplied to the airborne particle collector, and
the flow rate control device controls the amount of the liquid supplied from the liquid container to the airborne particle collector, based on the amount of the liquid detected by the liquid flow sensor.

5. The particle counting system according to claim 2, wherein
the flow rate control device, after completion of the collecting operation by the airborne particle collector, discharges the liquid from the airborne particle collector to the second flow path after the collection operation.

6. The particle counting system according to claim 5, wherein
the liquid supply and discharge system further includes a liquid flow sensor disposed in the first flow path and detecting the amount of the liquid supplied to the airborne particle collector, and
the flow rate control device controls the amount of the liquid supplied from the liquid container to the airborne particle collector, based on the amount of the liquid detected by the liquid flow sensor.

7. The particle counting system according to claim 2, wherein
the liquid supply and discharge system further includes a liquid flow sensor disposed in the first flow path and detecting the amount of the liquid supplied to the airborne particle collector, and the flow rate control device controls the amount of the liquid supplied from the liquid container to the airborne particle collector, based on the amount of the liquid detected by the liquid flow senor.

8. The particle counting system according to 1, wherein the flow rate control device causes the liquid container to supply the additional liquid while the airborne particle collector performs the collecting operation, and activates the pump to discharge the liquid from the airborne particle collector to the second flow path after the collecting operation. liquid flow sensor.

9. The particle counting system according to claim 8, wherein the liquid supply and discharge system further includes a liquid flow sensor disposed in the first flow path and detecting the amount of the liquid supplied to the airborne particle collector, and the flow rate control device controls the amount of the liquid supplied from the liquid container to the airborne particle collector, based on the amount of the liquid detected by the liquid flow sensor.

10. The particle counting system according to 1, wherein the flow rate control device, after completion of the collecting operation by the airborne particle collector, discharges the liquid from the airborne particle collector to the second flow path after the collection operation.

11. The particle counting system according to claim 10, wherein the liquid supply and discharge system further includes a liquid flow sensor disposed in the first flow path and detecting the amount of the liquid supplied to the airborne particle collector, and the flow rate control device controls the amount of the liquid supplied from the liquid container to the airborne particle collector, based on the amount of the liquid detected by the liquid flow sensor.

12. The particle counting system according 1, wherein the liquid supply and discharge system further includes a liquid flow sensor disposed in the first flow path and detecting the amount of the liquid supplied to the airborne particle collector, and the flow rate control device controls the amount of the liquid supplied from the liquid container to the airborne particle collector, based on the amount of the liquid detected by the liquid flow sensor.

* * * * *